(12) United States Patent
Jethmalani et al.

(10) Patent No.: US 7,560,499 B2
(45) Date of Patent: Jul. 14, 2009

(54) INITIATOR AND ULTRAVIOLET ABSORBER BLENDS FOR CHANGING LENS POWER BY ULTRAVIOLET LIGHT

(75) Inventors: Jagdish M. Jethmalani, San Diego, CA (US); Shiao H. Chang, Pasadena, CA (US); Robert H. Grubbs, Pasadena, CA (US)

(73) Assignee: Calhoun Vision, Inc., Pasadena, CA (US)

( * ) Notice: Subject to any disclaimer, the term of this patent is extended or adjusted under 35 U.S.C. 154(b) by 607 days.

(21) Appl. No.: 11/149,837

(22) Filed: Jun. 10, 2005

(65) Prior Publication Data

US 2006/0142528 A1 Jun. 29, 2006

Related U.S. Application Data

(63) Continuation-in-part of application No. 10/319,082, filed on Dec. 13, 2002, now abandoned.

(60) Provisional application No. 60/344,249, filed on Dec. 28, 2001.

(51) Int. Cl.
  *C08F 2/50* (2006.01)
  *C08J 3/28* (2006.01)
(52) U.S. Cl. .............................. 522/99; 522/34; 522/75; 522/148; 522/172
(58) Field of Classification Search .................. 623/6.6, 623/6.62, 6.16; 522/34, 75, 79, 99, 148, 522/172, 904; 523/106, 107, 108
See application file for complete search history.

(56) References Cited

U.S. PATENT DOCUMENTS

| | | | | |
|---|---|---|---|---|
| 4,391,963 A | | 7/1983 | Shirahata | |
| 4,477,326 A | * | 10/1984 | Lin | 522/21 |
| 4,585,693 A | * | 4/1986 | DeBergalis et al. | 428/324 |
| 4,636,431 A | * | 1/1987 | DeBergalis | 427/327 |
| 5,099,027 A | * | 3/1992 | Vogl et al. | 548/259 |
| 5,141,990 A | | 8/1992 | McKoy et al. | |
| 5,202,493 A | * | 4/1993 | Burk | 568/12 |
| 5,294,688 A | * | 3/1994 | Rehmer et al. | 526/260 |
| 5,559,163 A | * | 9/1996 | Dawson et al. | 522/75 |
| 5,712,324 A | * | 1/1998 | Lilly | 522/75 |
| 5,891,931 A | * | 4/1999 | Leboeuf et al. | 522/64 |
| 5,922,821 A | * | 7/1999 | LeBoeuf et al. | 526/286 |
| 6,153,760 A | * | 11/2000 | Kunzler | 548/259 |
| 6,187,835 B1 | * | 2/2001 | Szum et al. | 522/96 |
| 6,218,463 B1 | * | 4/2001 | Molock et al. | 524/720 |
| 6,399,734 B1 | * | 6/2002 | Hodd et al. | 528/32 |
| 6,482,757 B2 | * | 11/2002 | Vogt et al. | 442/133 |
| 6,737,496 B2 | * | 5/2004 | Hodd et al. | 528/32 |
| 6,851,804 B2 | * | 2/2005 | Jethmalani et al. | 351/159 |
| 2007/0055369 A1 | * | 3/2007 | Grubbs et al. | 623/6.6 |

FOREIGN PATENT DOCUMENTS

JP 57-207622 12/1982
JP 03-118069 5/1991

OTHER PUBLICATIONS

Japanese Notice of Rejection issued Jan. 7, 2008 during the prosecution of Japanese Patent Application No. 2003-558054.

* cited by examiner

*Primary Examiner*—Sanza L McClendon
(74) *Attorney, Agent, or Firm*—Fulbright & Jaworski L.L.P.

(57) ABSTRACT

Novel blends of photo-initiators and photo-absorbers are disclosed. By the proper selection of the type and amount of absorber and initiator used in a composition, it is possible to regulate the conditions under which photo-induced reactions occur. In a specific embodiment, blends of UV initiators and photoabsorbers are used to control the conditions under which UV initiated polymerization occurs.

14 Claims, No Drawings

INITIATOR AND ULTRAVIOLET ABSORBER BLENDS FOR CHANGING LENS POWER BY ULTRAVIOLET LIGHT

CROSS-REFERENCE TO RELATED APPLICATIONS

This Application is a Continuation-in-part of application Ser. No. 10/212,454 filed on Aug. 5, 2002. Ser. No. 10/212,454 claims priority to Provisional (35 USC 119(e)) application 60/344,248 filed on Dec. 28, 2001.

BRIEF SUMMARY OF THE INVENTION

The invention relates to a method for controlling the conditions under which photopolymerization occurs. The invention also relates to a novel blend of light absorbing compounds and photoinitiators which permits the selection of the conditions under which the photoinitiator induces photopolymerization.

BACKGROUND OF THE INVENTION

Photopolymerization is widely used to cure photopolymerizable compositions to produce fabricated articles. One recent application of photopolymerization is the development of optical elements whose optical properties can be changed through the use of photopolymerizable modifying composition dispersed within the optical element.

There exists a need, however, to control the conditions under which photopolymerization occurs. For example, in one embodiment of the optical element described above, intraocular lenses are first implanted into a patient and then adjusted post-operatively to achieve the refractive needs of the patient. This post-operative correction preferably occurs after wound healing is complete. This allows the surgeon to take into account any errors in the lens power calculation due to imprecise measurement or changes in the lens position that might occur due to the wound healing process.

The healing process may take up to several weeks, during which time it is necessary to avoid photopolymerization of the modifying composition. This requires that the patient shield his eyes from potential light sources that could cause photopolymerization. This severely restricts the patient's abilities to resume a normal routine after surgery.

Thus, it is desirable to control the conditions under which photopolymerization occurs at a predetermined set of conditions.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

SUMMARY OF THE INVENTION

The invention relates to a method of controlling the conditions under which stimulus-induced polymerization occurs. Specifically, it involves the use of blends of stimulus-absorbing compounds and stimulus-initiating compounds wherein the proportion of the two types of compounds are such that the initiation of polymerization is delayed until a desired set of conditions are reached.

In the preferred embodiment, a light-absorbing compound is used in conjunction with a photoinitiator to retard the action of the photoinitiator to a point that the absorbance of the light-absorbing compound has been reached. In a particularly preferred embodiment, the absorber compound is a UV absorber and the initiator is a UV initiator.

DETAILED DESCRIPTION OF THE INVENTION

The invention relates to a method of controlling the conditions under which photopolymerization occurs by blending a photoabsorber and a photoinitiator together with the monomers or macromers to the polymer matrix. By balancing the nature and relative proportions of the absorber and initiator, it is possible to control the conditions under which photopolymerization occurs.

A novel blend of photoabsorbers and photoinitiators is also provided. When the photoabsorber and photoinitiator are combined in desirable proportions, a novel composition for controlling photoinitiated photopolymerization is created. Using these novel blends it is possible to control the threshold intensity and wavelength of light required to induce polymerization. Similarly, the duration of exposure needed to induce polymerization can also be determined.

The photoabsorber composition used in the blend should absorb light in the same part of the spectrum that induces the photoinitiator to initiate polymerization. For example, if the photoinitiator is sensitive to ultraviolet light, the photoabsorbing component should be capable of absorbing ultraviolet light. If the photoinitiator is sensitive to infrared, then the photoabsorber must absorb infrared radiation. Photoinhibitors may also be used either in lieu or in addition to the photoabsorber. For example, in the case of ultraviolet (UV) light, photoinhibitors such as hindered amines, hydroquinones, methoxy phenols may be used. The light absorber used in the practice of the invention may also comprise a blend of one or more absorbers. For example, in the case of UV absorber, the UV absorber comprised may comprise a blend of UV absorbers which absorb light at different wavelengths.

Typical UV absorbers include benzotriazoles, benzophenones and the like. In the preferred embodiment, the photoabsorber is an ultraviolet (UV) absorber. One particularly useful class of UV absorbers is the benzotriazoles having the general structure:

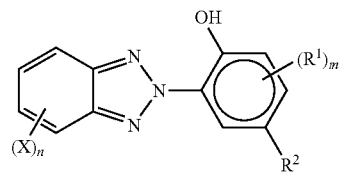

wherein X is independently selected from the group consisting of H, monovalent hydrocarbon radicals and monovalent substituted hydrocarbon radicals preferably containing 1 to about 8 carbon atoms, hydroxyl radicals, amino radicals, carboxyl radicals, alkoxy radicals and substituted alkoxy radicals, preferably containing 1 to 6 carbon atoms and halogen radicals; each $R^1$ is independently selected from the group consisting of H, alkyl radicals, substituted alkyl radicals, alkoxy radicals, substituted alkoxy radicals, preferably containing 1 to 8 carbon atoms, more preferably containing 1 to 4 carbon atoms, comprising either, or more hydroxyl radicals, amino radicals and carboxyl radicals, n is an integer of from 1 to 4 and m is an integer of from 1-3. Preferably, at least one of the X, $R^1$ is other than H. $R^2$ is selected from a moiety comprising vinyl, allyl, alkenyl, substituted alkenyl, alkenoxy, substitute alkenyoxy, acryloxy alkyl, substituted acryloxy, acrylate, methacrylate, and silicone.

Examples of useful monovalent hydrocarbon radicals include alkyl radicals, alkenyl radicals, aryl radicals and the like. Examples of useful alkoxy radicals include methoxy, ethoxy, propyoxy, butoxy, hexoxy and the like. Useful alkyls include methyl, ethyl, propyl, butyl, hexyl, octyl and the like. A particularly useful halogen is chlorine.

The substituted groups referred to herein are exemplified by the above noted groups (and the other groups referred to herein) substituted with one or more substituted groups including elements such as oxygen, nitrogen, carbon, hydrogen, halogen, sulfur, phosphorous and the like and mixtures or combinations thereof. Examples of useful amine groups include —$NH_2$ and groups in which one or both Hs is replaced with a group selected from monovalent hydrocarbon radicals, monovalent substituted hydrocarbon radicals and the like.

It is preferred that no more than one of the Xs is other than H and that no more than one of the $R^1$ is other than H. That is, it is preferred that all or all but one of the Xs be H and all or all but one of the $R^1$ be H. Such "minimally" substituted benzotriazole moieties are relatively easy to produce and provide outstanding ultraviolet-absorbing properties.

In lieu of ultraviolet absorbers, ultraviolet inhibitors may also be used. UV inhibitors which may be used in the practice of the invention include hindered amines, hydroquinones, methoxy phenones and the like. The compounds may be substituted for the UV absorbers described above.

A particularly useful class of UV-absorbing compounds is selected from compounds having the following formula or structure:

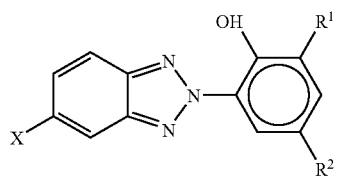

wherein X=chloro and $R^1$=tertiary butyl and $R^2$ has a vinyl group most preferred.

Examples of useful benzotriazoles include 2-(5-Chloro-2H-benzotriazole-2-yl)-6-(1,1-dimethylethyl)-4-ethenylphenol formula:

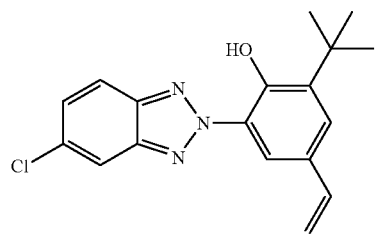

2-[2'-Hydroxy-3'-t-butyl-5'-(3"-dimethylvinylsilylpropoxy) phenyl]-5-methoxybenzotriazole being the formula:

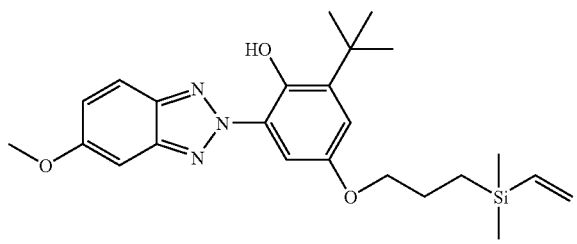

and 2-(2'-Hydroxy-3'-allyl-5'-methylphenyl)-2H-benzotriazole having the formula:

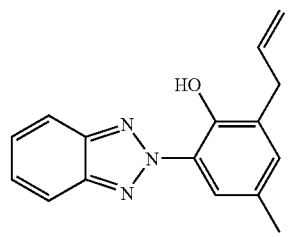

Another class of UV absorbers that are useful in the practice of the invention are benzophenones including but not limited to 4-allyoxy-2-hydroxy benzophenone having the general formula:

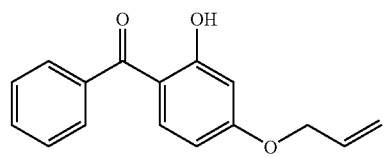

and 4,4'-dallyloxy-2,2'dihydroxybenzophenone having the general structure:

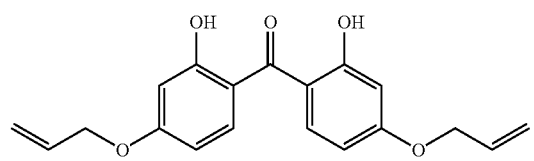

The preferred UV-absorbing compounds absorb UV light strongly in the range of 300 nm to 400 nm, and exhibit reduced absorption at wavelengths higher than about 400 nm.

The amount of UV absorber is that required to give the degree of light absorption desired and is dependent, for example, on the specific UV absorber used, the photoinitiator used, the composition of the element in which UV absorber is to be used, the macromers to be polymerized and the thickness, e.g., optical paths, of the element. By Beers Law of absorption, $A=\epsilon bc$, when $A$=absorbance, $\epsilon$=extinction coefficient, b=thickness or optical path, and c=concentration of the absorber. The required amount of absorber is inversely proportional to the optical path length or thickness. It is often desired that the UV light transmission at 400 nm be less than 10 to 15% of the incidental light, and at 390 nm be less than 3%.

As with the UV absorber, the preferred UV initiator useful in the practice of the invention are UV-sensitive UV initiators. Particularly preferred photoinitiators are x-alkylbenzoins having the general formula or structure:

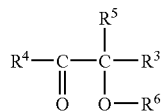

wherein $R^3$ is H, alkyl radical, aryl radical, substituted alkyl, or substituted aryl radical, and $R^4$ is H, alkyl radical, aryl radical, substituted alkyl or substituted aryl radical; $R^5$ and $R^6$ are phenyl or substituted phenyl allyl or allyloxy. Specific examples of $R^3$ and $R^4$ groups include methyl, phenyl trifluoropropyl, ethyl and cyano propyl. Phenyl substituents from the $R^5$ and $R^6$ groups may include alkyl, alkoxy, halogen, alkaryl, cyano alkyl, haloalkyl and N,N dialkyl amino. Photoinitiator useful in the practice of the invention include Irgacure 819, Irgacure 184, Irgacure 369 and Irgacure 651 all available from Ciba Specialty Chemicals Inc. Where clarity is required, such as in optical elements, Irgacure 651 is preferred.

Also useful in the practice of the invention are photoinitiators having one or more UV initiators bonded to a short polymer backbone or segment. This photoinitiator will have the general formula:

A-B-A$^1$ wherein in A and A$^1$ may be the same or different and are UV initiators and B as a short polymer segment comprising from 2 to 28 monomer moieties. While the formula recited above suggests that the UV initiators are attached at the end of the polymer chain in practice of this invention, the initiators can be bound at any point along the chain. In the case where the novel initiator is to be used as an optical element, the polymer backbone is the same general type of polymer as that used for the optical element. For example, where the optical element is fabricated from silicone polymer, the short polymer linking the initiators will also be a silicone polymer. Likewise, where the optical element is a polyacrylate based, the short polymer chain should be a polyacrylate.

In one embodiment, the photoinitiators comprise one or more UV initiators attached to a polysiloxane bridge and having the general formula:

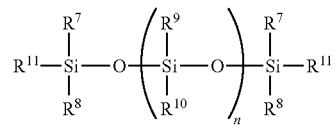

where $R^7$ through $R^{11}$ are independently selected from the group consisting of hydrogen, alkyls (primary, secondary, tertiary, cyclo), aryl or heteroaryl moieties and n is an integer from 2 to 28 and where at least one moiety $R^7$-$R^{11}$ is a UV initiator. In preferred embodiments, $R^7$-$R^{11}$ are $C_1$-$C_{10}$ alkyl or phenyl with methyl most preferred, but at least one should be hydrogen. One particularly useful silicon linked photoinitiator has the formula:

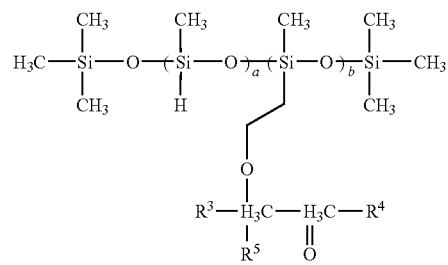

where $R^3$, $R^4$ and $R^5$ are as defined above and a and b are integers from 1 to 24 such that a and b is $\leq 24$.

The UV initiator is generally an UV sensitive photoinitiator with x-alkyl/benzoines described above preferred. Synthesis of the bridged UV initiator is described in U.S. Pat. No. 4,477,326.

In addition to the use of a bridged difunction photoinitiator, the UV absorber may also consist of one or more UV absorbers bonded by a short polymer bridge. The photoabsorber have the general formula

E-D-E$^1$ wherein E and E$^1$ are UV absorbers and D is a polymer chain with from 2 to 28 monomer moieties. While the formula recited above suggests that the UV absorbers are bonded to the ends of the polymer chains in practice of this invention, the absorber can be bonded at any point along the polymer chain. In addition, when the UV absorber contains more than one allyl or allyloxy groups, the UV absorber may be bonded to more than one polymer bridge. For example, a UV absorber with two allyl structures such as 4,4'diallyloxy, 2.2'-dihydroxy benzophenone may be linked to two polymer bridges. As with the initiator, the polymer bridge should be compatible with if not the same as the material used in the base composition.

In preferred embodiments, the UV absorber will have the general formula:

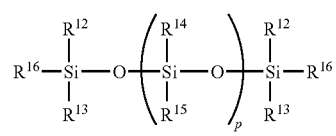

where $R^{12}$-$R^{16}$ and p is an integer from 1 to 26 are as defined above except that at least one moiety $R^{12}$-$R^{16}$ is a UV absorber and p is an integer from 1 to 26. One silicon bonded photoabsorber useful in the practice of the invention lens is the following structure:

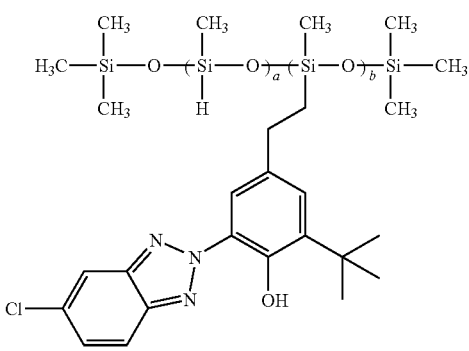

where a and b are integers from 1 to 24 and b is $\leq 24$.

Another UV absorber structure useful in the practice of the invention is a benzophenone linked to a siloxane backbone having the general formula:

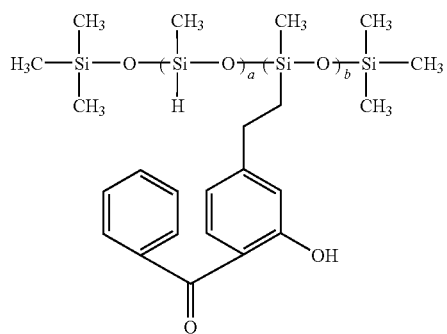

where a and b are integers from 1 to 24 and b is $\leq 24$.

In the case of a diallylbenzenphenone, the UV absorber may be linked to two polymer bridges such as two siloxane compounds.

The relative amounts of UV absorber and initiator will vary depending upon the desire degree of absorbance for the specific application. Generally the ratio of photoinitiator to UV absorber will range from about 1:1 to about 25:1, with 6:1 to 25:1 preferred. Generally, the relative amounts of photoinitiator and UV absorber can be calculated using the formula:

$$-\log T = A = \epsilon_1 b_1 c_1 + \epsilon_2 b_2 c_2$$

wherein T is transmittance, A is absorbance, $\epsilon_1$ is the extinction coefficient of the UV absorber, $b_1$ is the path length of the light and $c_1$ is the concentration of the UV absorber. $\epsilon_2$, $b_2$, and $c_2$ are as defined above except that they relate to the photoinitiator. In practice, it has been found that the actual absorbance is generally less than the predicted values such that the amount use should generally be at least 1.5 times the calculated amount.

The amounts of absorber and initiator can also be expressed in terms of the percent of the final composition. Using this reference, the amount of absorber present may range from 0.025 weight percent to 2 weight percent with 0.05 to 1.0 weight percent preferred. The amount initiator present may range from 0.05 to 0.5 weight percent. It will be understood by those skilled in the art that the actual amounts of each absorber and initiator used are dependent upon the nature of the initiator and absorber.

The photoinitiator and photoabsorber are combined with the polymers, monomers or macromers to be polymerized or crosslinked. In one embodiment, the photoinitiator is bound to the macromers. In other embodiments, the photoinitiator remains free in the mixture.

Monomers and macromers useful in the practice of the invention contain photopolymerizable functional groups. Typical photopolymerizable functional groups contain a group consisting of acrylate, allyloxy, cinnamoyl, methacrylate, stilbenyl and vinyl, with acrylate and methacrylate preferred.

The preferred macromers used in the practice of the invention are polysiloxanes or polyacrylate macromers endcapped with photopolymerizable groups.

Because of the preference for flexible and foldable IOLs, an especially preferred class of MC (Modifying Composition) monomers is polysiloxanes endcapped with a terminal siloxane moiety that includes a photopolymerizable group. An illustrative representation of such a monomer is:

wherein Y is a siloxane which may be a monomer, a homopolymer or a copolymer formed from any number of siloxane units, and X and $X^1$ may be the same or different and are each independently a terminal siloxane moiety that includes a photopolymerizable group. Illustrative examples of Y include:

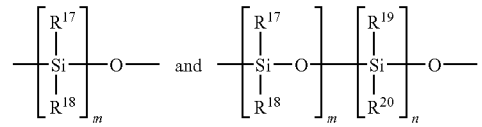

wherein: m and n are independently each an integer.

$R^{17}$, $R^{18}$, $R^{19}$, and $R^{20}$, are independently each hydrogen, alkyl (primary, secondary, tertiary, cyclo), aryl, or heteroaryl. In preferred embodiments, $R^{17}$, $R^{18}$, $R^{19}$, and $R^{20}$, is a $C_1$-$C_{10}$ alkyl or phenyl. Because MC monomers with a relatively high aryl content have been found to produce larger changes in the refractive index of the inventive lens, it is generally preferred that at least one of $R^{17}$, $R^{18}$, $R^{19}$, and $R^{20}$ is an aryl, particularly phenyl. In more preferred embodiments. $R^{17}$, $R^{18}$, $R^{19}$ are the same and are methyl, ethyl or propyl and $R^{20}$ is phenyl.

Illustrative examples of X and $X^1$ (or $X^1$ and X depending on how the MC polymer is depicted) are:

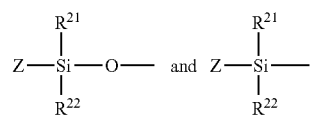

respectively wherein $R^{21}$ and $R^{22}$ are independently each hydrogen, alkyl, aryl, or heteroaryl; and Z is a photopolymerizable group.

In preferred embodiments $R^1$ and $R^6$ are independently each a $C_1$ and $C_{10}$ alkyl or phenyl and Z is a photopolymerizable group that includes a moiety selected from the group consisting of acrylate, allyloxy, cinnamoyl, methacrylate, stilbenyl, and vinyl. In more preferred embodiments, $R^{21}$ and $R^{22}$ is methyl, ethyl, or propyl and Z is a photopolymerizable group that includes an acrylate or methacrylate moiety.

In especially preferred embodiments, an MC monomer is of the following formula:

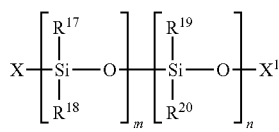

wherein X and $X^1$ are the same and $R^{17}$, $R^{18}$, $R^{19}$, and $R^{20}$ are as defined previously, and m and n as integers. Illustrative examples of such MC monomers include dimethylsiloxane-diphenylsiloxane copolymer endcapped with a vinyl dimethylsilane group; dimethylsiloxane-methylphenylsiloxane copolymer endcapped with a methacryloxypropyl dimethylsilane group; and dimethylsiloxane endcapped with a methacryloxypropyldimethylsilane group. Although any suitable method may be used, a ring-opening reaction of one of more cyclic siloxanes in the presence of triflic acid has been found to be a particularly efficient method of making one class of inventive MC monomers. Briefly, the method comprises contacting a cyclic siloxane with a compound of the formula:

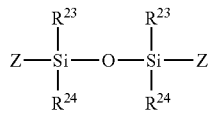

in the presence of triflic acid wherein $R^{23}$, $R^{24}$, and Z are as defined previously. The cyclic siloxane may be a cyclic siloxane monomer, homopolymer, or copolymer. Alternatively, more than one cyclic siloxane may be used. For example, a cyclic dimethylsiloxane tetramer and a cyclic methyl-phenylsiloxane trimer are contacted with bis-methacryloxypropyltetramethyldisiloxane in the presence of triflic acid to form a dimethyl-siloxane methyl-phenylsiloxane copolymer that is endcapped with a methacryloxylpropyl-dimethylsilane group, an especially preferred MC monomer.

The macromers useful in practice of the invention generally have a molecular weight (Mn) of from 500 to 30,000 with between 700 to 1000 preferred.

In one embodiment, the UV absorber, photoinitiator and a photopolymerizable modifying composition are dispersed within an optical element. When the element is exposed to a UV light source of sufficient intensity, the UV light exceeds the absorbance capacity of the UV absorber and stimulates the photoinitiator. The photoinitiator, in turn, induces polymerization of the modifying composition. The polymerization of the modifying composition causes changes in the optical properties of the element. When the UV source is removed or when the intensity falls below the absorbence capacity of the UV absorber, the polymerization reaction ceases, preventing further changes to the optical properties.

In the preferred embodiment, an intraocular lens ("IOL") is prepared from a first polymer matrix having a modifying composition dispersed therein. The modifying composition is capable of photoinduced polymerization. The IOL also contains a mixture of UV absorber and UV initiator as described above. The IOL is then implanted into a patient. After wound healing is complete, the optical power of the lens is then adjusted by exposing at least a portion of the lens to ultraviolet light for a sufficient time and intensity to cause the UV initiator to induce polymerization of the modifying composition. The photopolymerization of the modifying composition, in turn, causes changes in the optical properties of the IOL.

While the UV absorber/initiator blends of the invention are particularly useful in light adjustable optical elements, they can be used in any composition where it is desirable to delay a photoinitiated reaction until a prescribed level of intensity or dose at specified wavelengths has been met.

One example of this is UV curable compositions. Generally, care must be taken not to expose these compositions to ambient light because even at the low intensity of cure light (the UV light of the sun is about 6.0 milliwatts/cm$^2$) the photoinitiated curing reaction takes place. By adding sufficient UV absorber, the reaction can be delayed until the UV light intensity exceeds 6.0 milliwatts/cm$^2$.

EXAMPLES

The following examples are offered by way of example and are not intended to limit the scope of the invention in any manner.

Example 1

A series of siloxane slabs were prepared as reflected in Table 1 below. In the control experiments, Part A consisted of a silicone polymer MED 6820. Part B was prepared by mixing MED 6820 with a catalyst Pt-divinyltetramethyldisiloxane complex. Parts A and B were separately degassed to remove any air and then blended together. The mixture was then degassed and placed into a 1 mm thick mold where it was held in a Carver press for 24 to 48 hours at pressures up to about 1000 psi and at a temperature of about 37° C.

The experimental slabs were prepared in the same manner except that a blend of modifying composition, UV absorber and UV initiator was first prepared and then added to Part A. The proportions of the components were listed in Table I. The modifying composition (identified as CalAdd in Table 1) was methacrylate endcapped dimethylsiloxane diphenylsiloxane copolymer with a Mn from 700 to 1000 g mole$^{-1}$.

In the table below, the initiators used consisted generally of the following compounds, Irgacure 651, a commercially available UV initiator made by Ciba Specialty Chemicals, Inc.; Initiator B-pdms-B which is a blend of dual benzoin structures having the general structure:

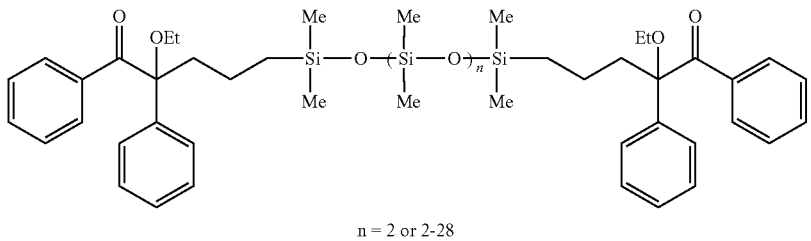

n = 2 or 2-28 wherein n ranges from 2 to 28, and B-L4-B which has the same general structure as above except with n=2 only. These initiators are preferred for applications where clarity is essential such as optical elements. In other applications where clarity is not essential, the use of other initiators such as Irgacure 369 is acceptable. Again, the key is to use an initiator that is triggered in the desire range of wavelengths and does not require an intensity in excess of prescribed safety limits for ophthalmic application purposes.

In the experiments recited in the table below, the ultraviolet absorbing compound used is UVAM, a commercially available absorber. While the use of UVAM is preferred, other ultraviolet absorbing compounds may be used.

In the experiments reported in Table 1, polymer slabs were prepared as described above. Sections of the slab were then taken and exposed to light at 365 nm for 30 to 120 minutes at intensities ranging from 0.01 to 8 milliwatts per square centimeters. The transmission and absorbance of the UV light through the section was determined by UV-visible spectrophotomer and Differential Photocalorimetric Analyzer, respectively, and reported in the table as wavelength ($\lambda$) at 10% Transmittance and $\Delta$ H (heat of polymerization).

TABLE 1

COMPOSITION OF EXPERIMENTAL SLABS AS A FUNCTION OF PHOTOPOLYMERIZATION CONDITIONS

| Experiment | Part A Wt % | Part B Wt % | Irg 651 Wt % | B-L4-B Wt % | B-pdms-B Wt % | UVAM Wt % | Cal.Add Wt % | Intensity mW/cm$^2$ | Environ | $\Delta$H J/g | $\lambda$ at 10% T |
|---|---|---|---|---|---|---|---|---|---|---|---|
| Control | 34.9 | 34.9 | 0.23 | | | | 29.97 | 4.82 | N$_2$ | −20.584 | 290 nm |
| | | | | | | | | 3.11 | Air | −18.586 | |
| 1 | 34.9 | 34.9 | 0.23 | | | 0.04 | 29.93 | 4.82 | N2 | −25.832 | 384 nm |
| | | | | | | | | 3.11 | Air | −11.575 | |
| 2 | 46.7 | 33.3 | 0.23 | | | 0.02 | 19.75 | 9.61 | N2 | −6.397 | 363 nm |
| | | | | | | | | 9.7 | Air | −8.742 | |
| 3 | 46.70 | 33.3 | 0.23 | | | 0.02 | 19.75 | 9.61 | N2 | −2.839 | 361 nm |
| | | | | | | | | 9.61 | Air | −8.156 | |
| 4 | 36.3 | 33.3 | 0.46 | | | 0.02 | 29.92 | 6.7 | N2 | 15.631 | 364 nm |
| | '' | '' | '' | | | '' | '' | 6.59 | Air | −21.363 | |
| | '' | '' | '' | | | '' | '' | 8.66 | Aqueous | −25.473 | |
| | '' | '' | '' | | | '' | '' | 6.77 | '' | −27.273 | |
| | '' | '' | '' | | | '' | '' | 6.37 | '' | −19.545 | |
| | '' | '' | '' | | | '' | '' | 4.33 | '' | −23.183 | |
| | '' | '' | '' | | | '' | '' | 087 | '' | −17.785 | |
| 5 | 36.3 | 33.2 | '' | | 0.5 | 0.02 | 29.98 | 6.68 | N2 | −18.36 | 323 nm |
| | '' | '' | | | '' | '' | '' | 6.68 | Air | −13.025 | |
| 6 | 36.2 | 33.1 | | | 0.75 | 0.03 | 29.82 | 7.49 | N2 | −20.231 | 364 nm |
| | '' | '' | | | '' | '' | '' | 3.74 | '' | −17.483 | |
| | '' | '' | | | '' | '' | '' | 7.49 | Air | −16.890 | |
| | '' | '' | | | '' | '' | '' | 3.74 | '' | −2.654 | |
| | '' | '' | | | '' | '' | '' | 7.96 | Aqueous | −19.147 | |
| | '' | '' | | | '' | '' | '' | 5.92 | '' | −21.672 | |
| | '' | '' | | | '' | '' | '' | 3.98 | '' | −20.231 | |
| | '' | '' | | | '' | '' | '' | 0.796 | '' | −21.880 | |
| 7 | 35.2 | 33.1 | | | .75 | .04 | 29.78 | 7.86 | Air | −10.275 | 383 nm |
| 8 | 36.1 | 33.1 | | | 1.0 | 0.04 | 29.76 | 7.86 | Air | −13.931 | 383 nm |
| | '' | '' | | | '' | '' | '' | 8.05 | Aqueous | −22.899 | |
| | '' | '' | | | '' | '' | '' | 6.26 | '' | −18.322 | |
| | '' | '' | | | '' | '' | '' | 5.92 | '' | −29.994 | |
| | '' | '' | | | '' | '' | '' | 4.03 | '' | −18710 | |
| | '' | '' | | | '' | '' | '' | 0.85 | '' | −11.459 | |
| 9 | 36 | 32.9 | 1.0 | | | 0.04 | 30.096 | 6.89 | Air | −10.015 | 387 nm |
| | '' | '' | '' | | '' | | | 3.56 | '' | −7.835 | |
| | '' | '' | '' | | '' | | | 3.45 | '' | −6.062 | |
| | '' | '' | '' | | '' | | | 2.07 | '' | −3.062 | |
| | '' | '' | '' | | '' | | | 7.36 | Aqueous | −20.009 | |
| | '' | '' | '' | | '' | | | 4.81 | '' | −18.071 | |
| | '' | '' | '' | | '' | | | 2.4 | '' | −15.171 | |
| | '' | '' | '' | | '' | | | 0.74 | '' | −11.869 | |

TABLE 1-continued

COMPOSITION OF EXPERIMENTAL SLABS AS A FUNCTION OF PHOTOPOLYMERIZATION CONDITIONS

| Experiment | Part A Wt % | Part B Wt % | Irg 651 Wt % | B-L4-B Wt % | B-pdms-B Wt % | UVAM Wt % | Cal.Add Wt % | Intensity mW/cm² | Environ | ΔH J/g | λ at 10% T |
|---|---|---|---|---|---|---|---|---|---|---|---|
|  | " | " |  | " |  |  |  | 0.01 | " | −9.219 |  |
| 10 | 36 | 32.9 |  | 1.0 |  | 0.04 | 30.096 | 6.98 | Air | −11.366 | 383 |
|  | " | " |  | " | " | " |  | 4.01 | " | −9.002 |  |
|  | " | " |  | " | " | " |  | 2.13 | " | −6.163 |  |
|  | " | " |  | " | " | " |  | 0.71 | " | −1.45 |  |
|  | " | " |  | " | " | " |  | 7.36 | Aqueous | −14.484 |  |
|  | " | " |  | " | " | " |  | 4.6 | " | −15.295 |  |
|  | " | " | " | " |  |  |  | 2.59 | " | −16.449 |  |
|  | " | " | " | " |  |  |  | 0.74 | " | −13.819 |  |
|  | " | " | " | " |  |  |  | 0.097 | " | −13.819 |  |

Example 2

A second series of siloxane slabs were prepared as reflected in Table 2 below. The slabs were prepared as described above except that two UV absorbers were used in the formula terms noted in Table 2. The absorber were UVAM (2-5 Chloro -2H-benzotriazole-z-yl)-6-[(1,1-dimethyl)-4-ethyl] phenol and dihydroxy benzophenone. The photoiniator used was BL4B described above. The slabs were evaluated in the manner described above with the results reported in Table 2.

TABLE 2

| Example # | Macromer Wt % | UVAM Wt % | D4BP Wt % | Photo-initiator Wt% | ΔHJ/g | Time (min.) at 25% completion of polymerization |
|---|---|---|---|---|---|---|
| 11 | 29.675 | 0.025 | 0.025 | 0.25 | −.28.586 | 6.7 |
| 12 | 29.015 | 0.0375 | 0.0375 | 0.25 | −.28.354 | 8.03 |
| 13 | 29.65 | 0.05 | 0.05 | 0.75 | −30.882 | 21.67 |
| 14 | 34.65 | 0.025 | 0.025 | 0.3 | −55.461 | 4.89 |
| 15 | 34.625 | 0.0375 | 0.0375 | 0.3 | −29.617 | 11.27 |
| 16 | 34.6 | 0.05 | 0.05 | 0.3 | −38.069 | 7.13 |
| 17 | 34.6 | .05 | .05 | 0.3 | −38.879 | 12.72 |

Example 3

An siloxane bridged benzoin was prepared in the following manner. In a 20 mL brown vial with a magnetic stirrer, 2.500 g of allyl benzoin, 0.376 g of tetramethyl divinyl disiloxane (SID4613.0 from Gelest) were weighed. The vial was sealed with a screw top with rubber septum and purged with argon for 5-7 minutes. The vial was then immersed in a 70° C. oil bath and the contents stirred using a magnetic stirrer. To the stirred mixture, 3 mL of toluene was added. The mixture was heated for 15-17 minutes at 70° C. while being stirred. To the stirred mixture, 50 μL of $H_2PtCl_6$ in THF was added. The rubber septum top was replaced with a regular screw top. The contents of the vial were stirred at 70° C. for 24 hours. An aliquot of the mixture was removed and silica gel TLC was run using hexane:ethyl acetate (95:5 & 97:3) to evaluate the completion of reaction. Although the reaction progress appeared complete, the reaction was run for another 18-24 hours. The reaction was stopped at ~44 hours.

Example 4

Flash column chromatography was run for the purification of the product of Example 3. A 25 inch long and 1 inch in diameter glass column with a 500 mL reservoir was used for purification. Dry silica gel (190 mL amount in 600 mL beaker) was transferred to fill the column to 17 inch height. 500 mL (485+15 mL) hexane:ethyl acetate (97:3 ratio) was used for packing the silica gel in the column. The packed silica gel now reached a height of 13.6 inches. The contents of the reaction mixture in Example 3 were loaded on to the top of the packed silica gel using an additional 3 mL of toluene. 500 mL (485+15 mL) followed by 200 mL (194+6 mL) hexane:ethyl acetate (97:3 ratio) was used for eluting the pure product. During the purification process, there were 66 fractions collected in 13×100 mm collection tubes. Silica gel TLC with hexane:ethyl acetate (97:3 and then 95:5 ratio) was run on each fraction. Based on the TLC analyses, there were IV major fractions that were separated during the flash chromatography process. Fractions 1 to 18 were combined to make Fraction I, fractions 19 to 25 were combined to make Fraction II, fractions 26 to 35 were combined to make Fraction III, and fractions 36 to 66 were combined to make Fraction IV. Out of these four fractions, only Fraction II was the pure compound, which was isolated by rotavap evaporation of the solvent and followed by vacuum drying for 18 hours. The total amount of Fraction II collected was 0.949 g, which corresponds to an overall yield of 35.4%. The UV-visible spectrophotometric property was determined on the Fraction II and it possessed about twice the absorbance as compared to the base benzoin alkyl at the same concentration confirming the structure.

Example 5

Another siloxane benzoin derivative was prepared according to the following procedure. In a 20 mL brown vial with a magnetic stirrer, 0.212 g of benzoin alkyl, 0.376 g of tetravinyl dimethoxy disiloxane (SIT7896.0 from Gelest) were weighed. The vial was sealed with a rubber septum screw top and purged with argon for 5-7 minutes. The vial was then immersed in a 70° C. oil bath and the contents stirred using a magnetic stirrer. To the stirred mixture, 3 mL of toluene was added. The mixture was heated for 15-17 minutes at 70° C. while being stirred. To the stirred mixture, 50 μL of $H_2PtCl_6$ in THF was then added. The rubber septum top was replaced with a regular screw top. The contents of the vial were stirred at 70° C. for an additional 24 hours. An aliquot of the mixture was removed and silica gel TLC was run using hexane:ethyl acetate (95:5 & 97:3) to evaluate the completion of reaction. Although the reaction progress appeared complete, the reaction was run for another 18-24 hours. The reaction was stopped at ~44 hours. In this case the product resulted in 4 benzoin alkyls being attached to the siloxane bridge.

Example 6

Flash column chromatography was run for the purification of the product of Example 6. A 25 inch long and 1 inch in diameter glass column with a 500 mL reservoir was used for purification. Dry silica gel (190 mL amount in 600 mL beaker) was transferred to fill the column to 17 inch height. 500 mL (485+15 mL) hexane:ethyl acetate (97:3 ratio) was used for packing the silica gel in the column. The packed silica gel now reached a height of 13.2 inches. The contents of the reaction mixture in Example 5 were loaded on to the top of the packed silica gel using an additional 3 mL of toluene. 500 mL (485+15 mL) hexane:ethyl acetate (97:3 ratio), 250 mL (237.5+12.5 mL) and 100 mL (95+5 mL) hexane:ethyl acetate (95:5 ratio) were added to the column sequentially to elute the pure product. During the purification process, there were 71 fractions collected in 13 x 100 mm collection tubes. Silica gel TLC with hexane:ethyl acetate (97:3 and then 95:5 ratio) was run on each fraction. Based on the TLC analyses, there were V major fractions that were separated during the flash chromatography process. The fractions 1 to 6 were combined to make Fraction I, fractions 7 to 9 were combined to make Fraction II, fractions 10 to 15 were combined to make Fraction III, fractions 16 to 33 were combined to make Fraction IV, and fractions 34 to 71 were combined to make Fraction V. Out of these five fractions, Fraction II was bi-functional compound, Fraction III was tri-functional compound and fraction IV was the pure tetra-functional compound. This pure compound (Fraction V) was isolated by rotavap evaporation of the solvent and followed by vacuum drying for 18 hours. The total amount of Fraction V collected was 0.950 g, which corresponds to an overall yield of 40.5%. The UV-visible spectrophotometric property was determined on the Fraction V and it possessed about four times the absorbance as compared to $BL_4$-H at the same concentration confirming the structure.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A blend of photoabsorber and photoinitiator wherein the photoabsorber is attached to a polysiloxane bridge having the general formula:

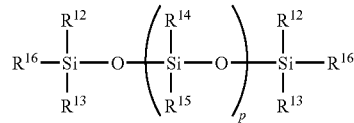

comprising one or more photoabsorbers bonded to at least one polysiloxane bridge through $R^{12}$, $R^{13}$, $R^{14}$, $R^{15}$ and/or $R^{16}$ wherein the rest of the $R^{12}$, $R^{13}$, $R^{14}$, $R^{15}$ and/or $R^{16}$ are selected from group consisting of hydrogen, alkyls, aryl or heteroaryl moieties;

p equals 2-28;

the photoinitiator is attached to a polysiloxane bridge having the general formula:

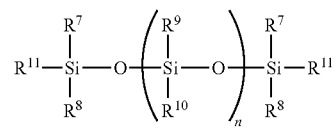

comprising one or more photoinitiators bonded to at least one polysiloxane bridge through $R^7$, $R^8$, $R^9$, $R^{10}$ and/or $R^{11}$ wherein, the rest of the $R^7$, $R^8$, $R^9$, $R^{10}$ and/or $R^{11}$ are selected from the group consisting of hydrogen, alkyls, aryl and heteroaryl moieties;

n equals 2-28.

2. The blend of claim 1 wherein the photoabsorbers have the general formula:

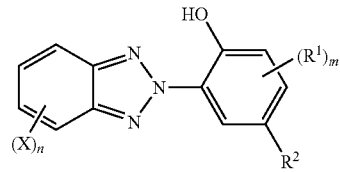

wherein X is independently selected from the group consisting of H, monovalent hydrocarbon radicals and monovalent substituted hydrocarbon radicals containing 1 to about 8 carbon atoms, hydroxyl radicals, amino radicals, carboxyl radicals, alkoxy radicals and substituted alkoxy radicals;

$R^1$ is independently selected from the group consisting of H, alkyl radicals, substituted alkyl radicals, alkoxy radicals, substituted alkoxy radicals, containing 1 to 8 carbon atoms $R^2$ comprises a reactive functionality for connecting the photoabsorber to the polysiloxane bridge and is selected from the group consisting of alkenyl, substituted alkenyl, alkenoxy, substituted alkenoxy, acryloxy alkyl and substituted acryoxy alkyl;

n is an integer of from 1 to 4 and m is an integer of from 1-3; and the photoinitiators have the general formula:

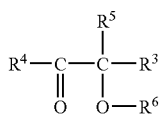

wherein $R^3$ and $R^4$ are H, alkyl radical, aryl radical, substituted alkyl, or substituted aryl radical;

$R^5$ is a phenyl or substituted phenyl; and $R^6$ comprises a reactive functionality for connecting the photoinitiator to the polysiloxane bridge and is selected from the group consisting an allyl and an allyloxy group.

3. The blend of claim 1 wherein $R^7$, $R^8$, $R^9$ and/or $R^{10}$ of the polysiloxane bridge are independently selected from the group consisting of alkyls, aryl and heteroalkyl moieties.

4. A blend of a silicon bonded photoabsorber and a silicon bonded photoinitiators wherein the a silicon bonded photoinitiator has the general formula:

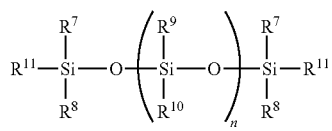

comprising one or more photoinitiators bonded to at least one polysiloxane bridge through $R^7$, $R^8$, $R^9$, $R^{10}$ and/or $R^{11}$;

n equals 2-28;

wherein at least one of $R^7$-$R^{11}$ is a photoinitiator having the general formula:

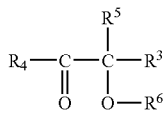

wherein $R^3$ is H, alkyl radical, aryl radical, substituted alkyl, or substituted aryl radical, and $R^4$ is H, alkyl radical, aryl radical, substituted alkyl or substituted aryl radical; $R^5$ is a phenyl or substituted phenyl and $R^6$ comprises a reactive functionality for connecting the photoinitiator to the polysiloxane bridge and is selected from the group consisting of an allyl and an allyloxy group;

wherein $R^7$, $R^8$, $R^9$, $R^{10}$ and/or $R^{11}$ are independently selected from the group consisting of hydrogen, alkyls, aryl, heteroalkyls, and a silicon bonded photoabsorber having the general formula

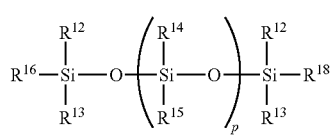

wherein at least one of $R^{12}$ to $R^{16}$ is a photoabsorber having the formula:

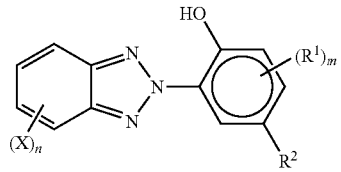

wherein X is independently selected from the group consisting of H, monovalent hydrocarbon radicals and monovalent substituted hydrocarbon radicals containing 1 to about 8 carbon atoms, hydroxyl radicals, amino radicals, carboxyl radicals alkoxy radicals and substituted alkoxy radicals, and each $R^1$ is independently selected from the group consisting of H, alkyl radicals, substituted alkyl radicals, alkoxy radicals, substituted alkoxy radicals and $R^2$ comprises a reactive functionality for connecting the photoabsorber to the polysiloxane bridge and is selected from the group comprising vinyl, allyl, alkenyl, substituted alkenyl, alkenoxy, substitute alkenyoxy, acryloxy alkyl, substituted acryloxy, acrylate, methacrylate, and silicone, n in the photoabsorber formula is an integer of from 1 to 4 and m is an integer of from 1 to 3.

5. The blend of claim 1 wherein the photoabsorber is a benzophenone and is bonded to the polysiloxane bridge through $R^{12}$, $R^{13}$, $R^{14}$, $R^{15}$ and/or $R^{16}$.

6. The blend of claim 5 wherein the benzophenone has the structure:

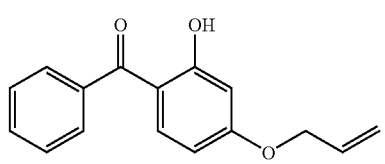

7. The blend of claim 5 wherein the benzophenone has the formula:

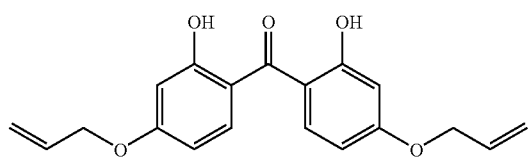

8. The blend of claim 4 wherein the photoabsorber is a benzotriazole.

9. The blend of claim 8 wherein the photoabsorber has the formula:

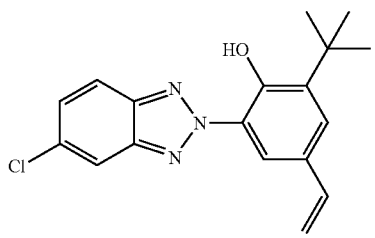

10. The blend of claim 8 wherein the photoabsorber has the formula:

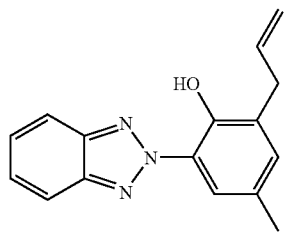

11. The blend of claim 4 wherein the photoinitiator is allylic benzoin and is bonded to at least one polysiloxane bridge through $R^7$, $R^8$, $R^9$, $R^{10}$ and/or $R^{11}$.

12. The blend of claim 2 wherein X contains 1 to 6 carbon atoms and halogen radicals.

13. The blend of claim 2 wherein $R^1$ contains 1 to 4 carbon atoms and comprises a hydroxyl radical, amino radical and or carboxyl radical.

14. The blend of claim 4 wherein X contains 1 to 6 carbon atoms and comprises halogen radicals.

* * * * *